US005647060A

United States Patent [19]
Lee

[11] Patent Number: 5,647,060
[45] Date of Patent: Jul. 15, 1997

[54] PROTECTIVE REPLACEABLE FACE SHIELD ASSEMBLY

[76] Inventor: Janet W. Lee, 9043 N. 87th Way, Scottsdale, Ariz. 85258

[21] Appl. No.: 562,111

[22] Filed: Nov. 22, 1995

[51] Int. Cl.$^6$ ................................................. A61F 9/04
[52] U.S. Cl. ................ 2/9; 2/12; 2/424; 128/857
[58] Field of Search ........................ 2/10, 9, 8, 424, 2/425, 12, 427; 128/857, 858, 863

[56] References Cited

U.S. PATENT DOCUMENTS

| | | | |
|---|---|---|---|
| 2,758,307 | 8/1956 | Treiber | 2/8 X |
| 2,874,387 | 2/1959 | Bannister et al. | 2/10 X |
| 4,117,553 | 10/1978 | Bay | 2/10 |
| 4,305,160 | 12/1981 | Sundahl | 2/424 |
| 4,701,965 | 10/1987 | Landis | 2/9 X |
| 4,986,282 | 1/1991 | Stackhouse et al. | 128/858 X |
| 5,347,655 | 9/1994 | Garrett | 2/10 |

*Primary Examiner*—Peter Nerbun
*Attorney, Agent, or Firm*—Gregory J. Nelson

[57] ABSTRACT

A face shield assembly to protect the wearer from contaminants and airborne particles. The shield assembly includes a visor having a head-engaging band and a forwardly extending bill portion which, in the preferred embodiment, defines a light passing area which in the preferred form of the invention comprises a plurality of apertures. The band carries attachment means in the form of outwardly extending studs which engage arcuate slots and apertures in the transparent shield. The transparent shield is fabricated from a flexible plastic and in a use-position is spaced from the face of the wearer and extends above and below the visor for protection. The attachment means allow the visor to be pivoted upwardly to an out-of-the-way position when the headband is in place on the wearers head. The apertures also permit air circulation for the comfort of the wearer and to minimize fogging of the shield.

11 Claims, 2 Drawing Sheets

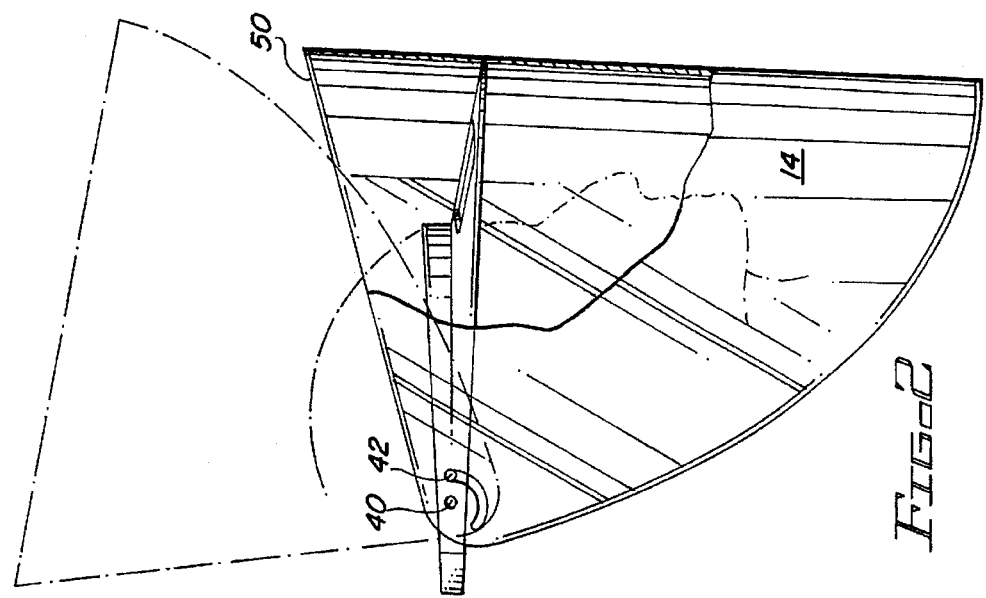
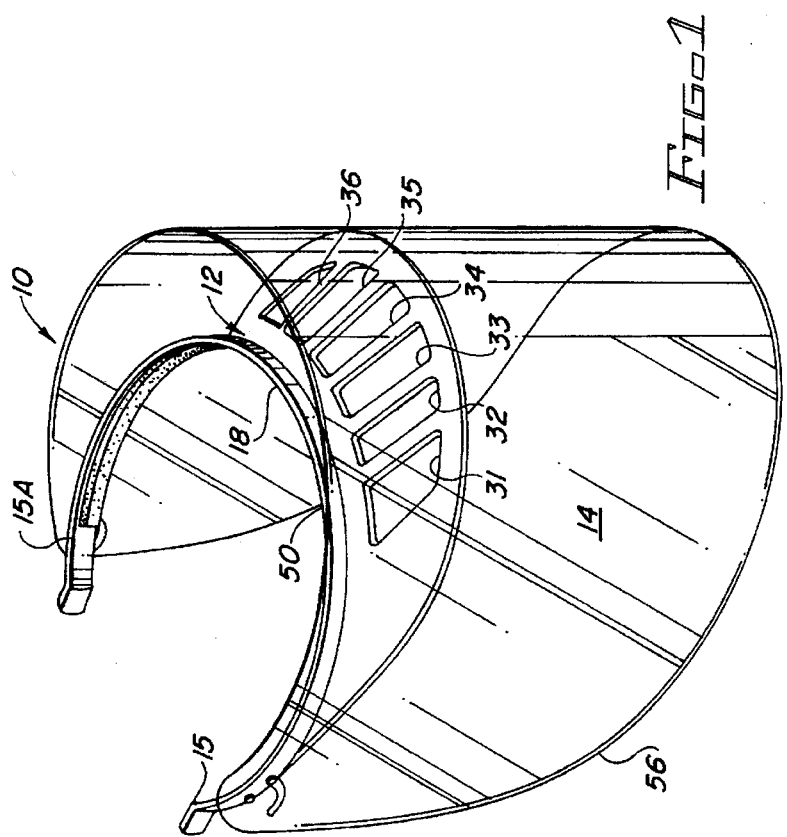
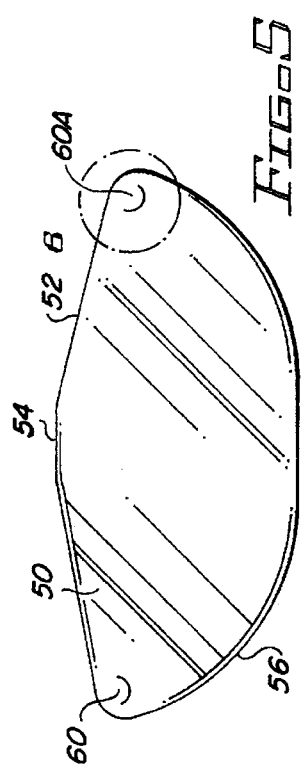

PROTECTIVE REPLACEABLE FACE SHIELD ASSEMBLY

BACKGROUND OF THE INVENTION

1. Field of the Invention

The present invention relates to a face shield assembly and more particularly relates to the type of face shield assembly that may be worn by workers for eye protection and also by medical personnel for eye protection and also to minimize the possibility of cross contamination with patients.

Various types of protective face shields can be found in the prior art. The early patent to Lang et al, U.S. Pat. No. 797,293 discloses a face shield which protects the wearer from dust having a shield of resilient transparent material carried on a frame to support the shield spaced from the forehead of the wearer. The shield has perforations in the supporting bridge which are screened to permit ventilation but serves to keep dust particles from entering the area near the user's face.

U.S. Pat. No. 2,262,449 shows what the patentee terms as a "Head Wind Shield" for use by motorcyclists to protect the face against wind, rain and dust when motoring. A transparent face shield formed of a celluloid or other transparent material is secured to a band which is in swivel engagement with a head-encircling band to allow the shield to be raised.

U.S. Pat. No. 3,152,588 shows a safety facial mask which is a one-piece transparent mask adapted to fit the contours of the face having a screen for filtering air breathed by the wearer. The patentee states the mask may be used for protection during beauty treatments or while performing household or industrial tasks in dusty or spray-laden environments.

U.S. Pat. No. 4,475,254 shows a visor attachment for a helmet shield which has a flexible polymeric visor attachable to one edge portion of the helmet shield. The visor has a visor bill and a support portion. The support portion has an arcuate section shaped to conform to the contour of the shield when flexed. Means are provided to attach the visor support portion to a shield for converting a shield to a visor/shield combination which means include special tongues for grasping the edge of the shield when clips for locking the visor to the shield are snapped over each tongue on the visor support portion and over one side of the shield to bind the shield to the tongues.

U.S. Pat. No. 471,965 relates to a visor type mask for use by dentists and dental personnel. The mask protects the dentist from handpiece splatter and the mask has a visor which attaches to the wearer's head above the eyes and supports a transparent shield which extends from the visor downwardly below the wearer's mouth. The shield is detachable from the visor at snaps for cleaning and replacement. The visor has a vent for air circulation which may be closed by a cover for protection. A filter may be applied to the shield for eye protection when ultraviolet light is used by the wearer.

Thus, as indicated by the foregoing, the prior art suggests various constructions for face protecting shields or masks. While these often involve some type of head-engaging band from which the visor is supported, the prior art shields are often unwieldy to use and expensive to manufacture. Further, the prior art shields are often of a design which does not encompass a sufficient part of the wearer's head to provide adequate protection. Also, many of the prior art devices are constructed in a manner which blocks or prevents light from entering the area within the shield shading the wearer's face and working area.

SUMMARY OF THE INVENTION

Briefly, the present invention provides an improved protective face shield assembly which has a visor component having a head band with bridge and opposite temple portions and rearwardly extending tabs to facilitate positioning and removal of the assembly. The visor has a forwardly extending visor bill having a plurality of cut-outs which promote air circulation and allow light to pass through the apertures to illuminate the user's face and the work area. A face shield fabricated from a transparent polymeric material is detachably secured to the visor component. The face shield has a pair of apertures at either side which are engageable in fastener studs extending outwardly from opposite temple portions of the head band. One of the apertures in the shield is arcuate which permits the visor to be pivoted upwardly away from the face of the wearer. The visor shield is also dimensioned so that it extends vertically around the edges of the visor to fully protect the wearer and also extends vertically a substantial distance above the edge of the visor. The shield may be cut or stamped from a suitable transparent polymeric material and is provided to the user in a flattened condition and, as indicated above, the shields may be replaced by connecting the shield to the fastener studs at side of the visor head band.

Accordingly, it is a broad object of the present invention to provide a protective face shield assembly with a replaceable shield which will protect the wearer from airborne dust, debris, metal burrs, wood chips, contaminants and the like.

It is a more specific object of the present invention to provide a new and improved face shield assembly for use by medical personnel such as dentists and surgeons to protect them from cross-contamination from blood and body fluids, bone particles and the like which may be discharged into the air when working on a patient.

Another object of the present invention is to provide a protective face shield assembly which has a shield portion which may be easily removed and replaced in the event it becomes scratched and which may also be a one-use item for hygienic purposes.

BRIEF DESCRIPTION OF THE DRAWINGS

The above and other objects and advantages of the present invention will be more fully understood and appreciated from the following description, claims and drawings in which:

FIG. 1 is a perspective view of the shield assembly of the present invention;

FIG. 2 is a side elevational view of the shield assembly of the present invention showing the head and face of a wearer;

FIG. 5 is a plan view showing the shield portion of the assembly as provided in a flattened or planar condition.

Figure 3:
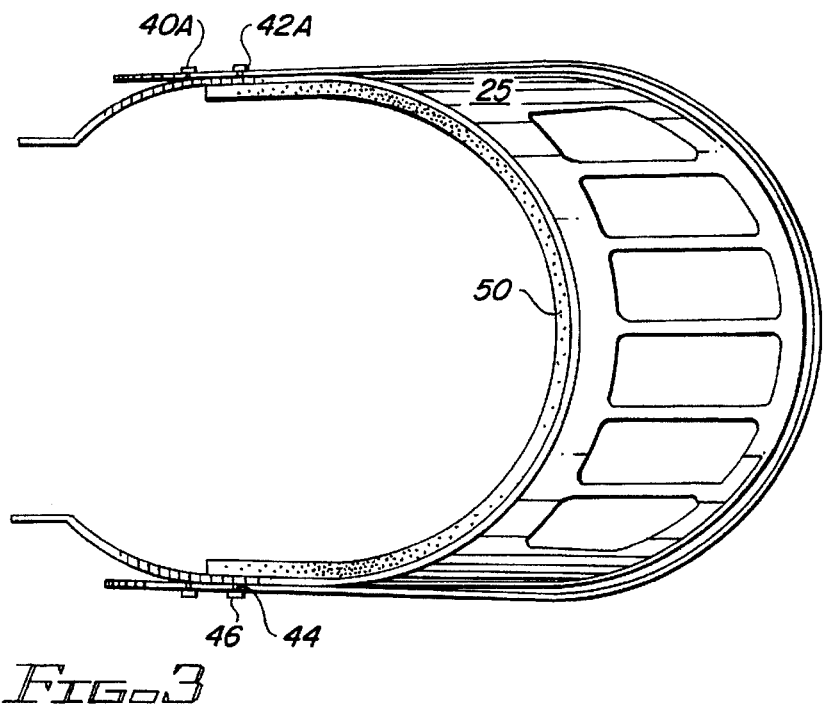
FIG. 3 is a top view thereof.

The shield assembly of the present invention is generally designated by the numeral 10 and is comprised of two components, a visor 12 and a shield 14. The visor supports the removable, replaceable shield protecting the face of the wearer. The visor 12 consists of a resilient band having opposite temple band portions 15 and 15A which are interconnected at their forward end by a bridge 18. The distal ends of the temple band portions 15 and 15A terminate rearwardly extending tabs 20 and 20A which assist the user in placing the visor on the head and removing the visor from the head of the wearer. To position or remove the assembly, the user may conveniently grasp the tabs 20, 20A to outwardly flex the temple bands 15, 15A.

A visor bill 25 is integrally formed with the visor band and has an edge 28 which extends forwardly from the opposite temple section and has a curved forward edge section. The bill may have an overall depth of approximately 2 to 4 inches. A plurality of apertures 30, 31, 32, 33, 34 and 35 are provided in the visor bill 25. The apertures occupy a substantial portion of the visor area extending from adjacent the opposite sides of the visor having a depth slightly less than the depth of the visor. The apertures may be shaped and arranged in any aesthetically pleasing manner which permits passage of light through the bill to eliminate shadows on the work area.

Attachment means 40 and 42 and 40A and 42A are provided on the rear portion of the opposite temple sections 15, 15A of the visor band. The attachment means are in form of small studs or projections each having a shaft 44 and enlarged head 46 which are integrally formed with the visor band. In fact, the entire visor band consisting of the head band, visor and attachment means may be integrally formed from a suitable plastic by injection molding. Plastics such as polycarbonates and polyethylene are preferred materials and the material sold under the trademark Lexan® works well.

For the comfort of the wearer, a strip of polymeric foam material 50 may be adhered to the interior surface of the band to cushion contact between the band and the head of the wearer and also to absorb moisture.

The second component of the shield assembly of the present invention is the shield 14. The shield 14 may be fabricated from any suitable transparent material. Typically the material would have a thickness of approximately 0.10–0.40 mm. so that the shield has sufficient strength yet is still flexible. The shield may be initially formed by stamping or cutting from a flat sheet of stock material. The shield as formed is flat and is normally provided to the user in this condition as seen in FIG. 5 with a peelable protective covering which is removed at the time of use. The shield 14 has an upper edge which is defined by two slightly converging rectilinear edge sections 50 and 52 which are intersected by a generally horizontal section 54. The lower edge 56 of the shield is generally arcuate extending from the ends of sections 50 and 52. The corners defined by the intersection of edge sections 50, 52 and 56 may be slightly rounded as shown for safety and to provide a more pleasing appearance.

Figure 6:
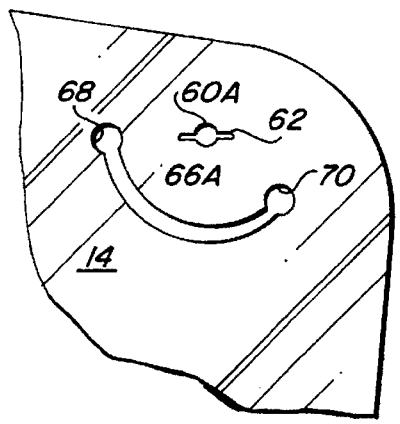
FIG. 6 is a detailed view of the mounting slots provided in the opposite corners of the shield as seen in FIG. 5.

As best seen in FIGS. 5 and 6, the shield 14 is provided with fastening means. The fastening means comprise a first pair of apertures 60 and 60A which are provided in the opposite corners. The apertures 60, 60A are shown as being generally circular and being diametrically intercepted by a slot 62. An arcuate slot 66 extends generally circumferentially with respect to slot 60 and a similar arcuate slot 66A extends circumferentially adjacent aperture 60A. Slots 66, 66A have a width slightly greater than the diameter of the shaft 44 of studs 42 and 42A. Arcuate slots 66, 66A are each provided with an enlarged bore 68 and 70 at their opposite ends which bores have a diameter somewhat greater than the head 46 on mounting studs 40 and 40A on the headband.

The components are assembled by engaging the shield 14 to the visor 12. This is accomplished by inserting studs 40 and 40A through apertures 60 and 60A, respectively. Similarly, studs 42 and 42A are inserted through the enlarged ends 68 of slots 66 and 66A, respectively. Thus, the attachment of the shield to the visor is a simple procedure and the heads of the studs retain the shield in place. The shield 14 may be removed for replacement of a new shield by simply detaching or unsnapping the studs from the associated apertures at the sides of the shield.

As best seen in FIGS. 1 and 2, with the components assembled in the normal use-position, the upper edge sections 50 and 52 of the shield extend forwardly and upwardly to a location well above the visor bill. Similarly, the curved edge 56 extends downwardly to a position that would normally be at least co-extensive with or below the mouth and chin area of the wearer. Although it will be apparent that the shape of the shield may vary to some extent, it is important that the shield cover the eyes, nose and mouth area of the user and also extend upwardly above the visor bill to protect the bill so that the apertures 30 to 35 are protected from dust, chips and detritus. The head of the wearer is also protected and it is noted that the shield extends about 180° wrapping to the sides of the face. By way of example, the upper edge of the shield would normally extend at least 1" to 2" above the visor bill. The shield, as indicated, is made from a resilient transparent material such as Lexan® which has good optical qualities and is reasonably resistant to scratching. In certain applications, the shield may be cleaned and re-used and discarded only when vision through the transparent shield becomes obstructed. In surgical applications, the shield would normally be discarded after a single use similar to latex gloves commonly used by dentists and medical personnel, whereas for in-office medical use the shield may be disinfected and re-used.

When the shield is in use, it is positioned as shown in FIGS. 1 and 2, covering the face area of the user and also protecting the apertures in the bill from entry of contaminants or irritants. The visor is spaced forwardly from the face of the user so that fogging is avoided under most normal conditions and the shield will not impair or impede the normal breathing of the user. The generous spacing also allows the user to comfortably wear prescription eyeglasses or optical loops beneath the shield. Since the visor bill is provided with apertures 31 to 35, circulation along the interior surface of the shield is promoted which enhances breathing and minimizes possible fogging. Also, another significant advantage of the visor assembly according to the present construction, is that the apertures in the visor bill permit light from above to pass through the apertures, reducing shadowing that would normally occur with conventional visor bill structures. Since medical personnel, such as dentists, often work with lights which are oriented above the patient and the medical personnel, light permeability of the bill is a significant advantage as shadowing of the work area is minimized.

The unique fastening arrangement not only allows easy attachment and removal of the visor shield but also facilitates convenient pivotal movement of the visor by the wearer. The wearer may continue to wear the visor assembly between patients or when not engaged in activities which pose a danger to the wearer such as grinding or sanding. In this case, the wearer may simply grasp the lower edge of the visor shield and move it upward to the position shown in phantom lines in FIG. 2. The shield will pivot about the rear studs 40 and 40A and upward pivotal movement will be facilitated by the arcuate slots 66 and 66A.

Figure 4:
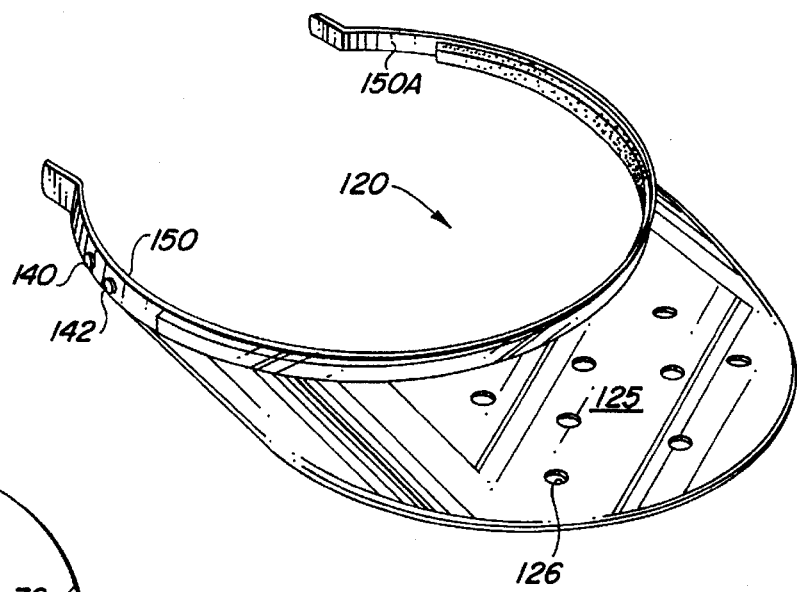
FIG. 4 is a perspective view of an alternate embodiment of the visor portion of the shield assembly.

FIG. 4 shows an alternate embodiment of the visor component of the present invention which has been designated with the numeral 120. The visor 120 is generally constructed as it has been described with reference to FIG. 1 having opposite temple band sections 150 and 150A which support a forwardly extending visor bill 125. Mounting studs 140 and 142 project from the outer surfaces of the band for attachment of a shield component 14 as has been described above. In the embodiment shown in FIG. 4, the visor is constructed having at least the visor bill portion 125 formed from a transparent or translucent material such as a clear plastic which will allow light to pass through the visor bill to the area behind the shield. It will also be possible to fabricate the bill from an opaque material having a transparent or translucent inset therein in the visor bill. It is preferred that the bill have apertures 126 therein as shown to promote ventilation.

From the foregoing, it will be seen that the present invention provides a safety shield assembly which may be used in both medical and non-medical applications. The shield assembly is effective, convenient to use and inexpensive to manufacture. The unique design protects the full face area of the user and also promotes passage of air and light to the area between the interior of the shield and the user's face. The user may easily replace shields when necessary or when required by good hygenic practice. The shield can be easily pivoted to an elevated position away from the face of the user when the shield is not necessary.

It will be obvious to those skilled in the art to make various changes, alterations or modifications to the invention described herein. To the extent these various changes, alterations or modifications do not depart from spirit and scope of the appended claims, they are intended to be encompassed therein.

I claim:

1. A protective face shield assembly to be worn on the head of the wearer comprising:
   (a) a visor having a head-engaging band with a forwardly extending visor bill, said bill defining a light passing area;
   (b) projection means on said head-engaging band at opposite locations; and
   (c) a substantially transparent shield defining apertures selectively engageable with said projection means to detachably secure said shield to said visor in a position to selectively allow the wearer to pivot the shield from a first use-position spaced in front of the wearer's face and a second position with the shield disposed substantially above the face of the wearer and whereby said shield may be removed from said visor by disengaging said projection means from said apertures.

2. The protective face shield of claim 1 wherein said light-passing area comprises a plurality of apertures in the said visor.

3. The protective face shield of claim 1 wherein said head-engaging band comprises spaced-apart resilient temple sections interconnected by a curved forward section and wherein the terminal ends of said temple sections have rearwardly extending tabs.

4. The protective face shield of claim 3 wherein said band is molded from plastic.

5. The protective face shield of claim 2 wherein said shield is dimensioned so when secured to said visor the shield extends substantially above the visor to protect said apertures and said shield extends below the visor to an area approximately corresponding to the area of the chin of the wearer when in a use-position.

6. The protective face shield of claim 3 wherein said head band includes cushioning means on an interior surface of at least the curved forward section.

7. The protective face shield of claim 1 wherein said apertures comprise a first generally circular aperture and a second generally arcuate aperture disposed adjacent said first aperture whereby said studs may be engaged in and disengaged from said apertures.

8. The protective face shield of claim 1 wherein said shield is fabricated from a clear flexible plastic material.

9. The protective face shield of claim 1 wherein said visor is comprised of a plastic material.

10. A protective face shield assembly for medical, industrial and dental personnel comprising:
    (a) a visor having a head-engaging band, said band having opposite resilient temple band sections connected by a forward bridge, said head band having an integrally formed forwardly-extending bill defining a plurality of apertures therein which occupy a substantial portion of the visor bill area;
    (b) a transparent shield having an upper edge and lower and side edges, said shield defining an aperture and an arcuate slot oppositely located along each of the side edges thereby defining a pair of apertures and slots;
    (c) said head band having a pair of studs located on each of the temple bands engageable in said apertures and slots to detachably secure said shield to said visor in a first use-position with the shield extending about the face area of the wearer and substantially above the visor bill and whereby said shield is pivotal at said studs to a non-use position disposed above the face of the wearer and whereby said shield may be removed from said visor by disengaging said studs from said apertures.

11. The protective face shield of claim 10 wherein said arcuate slots include detent locations at the opposite ends thereof.

* * * * *